United States Patent
Penna et al.

(10) Patent No.: US 9,913,643 B2
(45) Date of Patent: Mar. 13, 2018

(54) INTERLOCK ASSEMBLIES FOR REPLACEABLE LOADING UNIT

(71) Applicant: Covidien LP, Mansfield, MA (US)

(72) Inventors: Christopher Penna, Guilford, CT (US); Patrick Mozdzierz, Glastonbury, CT (US); Paul Scirica, Huntington, CT (US); Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 617 days.

(21) Appl. No.: 14/273,850

(22) Filed: May 9, 2014

(65) Prior Publication Data

US 2015/0320420 A1    Nov. 12, 2015

(51) Int. Cl.
*A61B 17/072*    (2006.01)
*A61B 17/115*    (2006.01)
*A61B 17/00*    (2006.01)

(52) U.S. Cl.
CPC ........ *A61B 17/072* (2013.01); *A61B 17/1155* (2013.01); *A61B 2017/00473* (2013.01); *A61B 2017/07271* (2013.01)

(58) Field of Classification Search
CPC .............. A61B 17/072; A61B 17/1155; A61B 2017/0727; A01B 12/006
USPC .................. 227/19, 176.1; 606/153
See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev | |
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |
| 4,289,133 A | 9/1981 | Rothfuss | |
| 4,304,236 A * | 12/1981 | Conta ............... A61B 17/115 227/179.1 |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |

(Continued)

FOREIGN PATENT DOCUMENTS

| | | |
|---|---|---|
| CA | 908529 | 8/1972 |
| CN | 101856251 A | 10/2010 |

(Continued)

OTHER PUBLICATIONS

European Search Report issued in corresponding European Appln. No. EP 15166899.3 dated Feb. 3, 2016.

(Continued)

*Primary Examiner* — Nathaniel Chukwurah

(57) ABSTRACT

Interlock assemblies for attaching a loading unit to a surgical stapling instrument are provided. The interlock assemblies are formed on a proximal end of a shell member and on a distal end of an adapter assembly. The interlock assemblies may include a collar member for selectively securing the shell member to the adapter assembly. The collar member may be mounted on the shell member or on the adapter assembly.

10 Claims, 14 Drawing Sheets

(56) References Cited

U.S. PATENT DOCUMENTS

| | | |
|---|---|---|
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A * | 9/1994 | Main .................... A61B 17/115 227/179.1 |
| 5,355,897 A | 10/1994 | Pietrafitta et al. |
| 5,360,154 A | 11/1994 | Green |
| 5,368,215 A | 11/1994 | Green et al. |
| 5,392,979 A * | 2/1995 | Green .................. A61B 17/115 227/179.1 |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,549,637 A | 8/1996 | Crainich |
| 5,553,675 A | 9/1996 | Pitzen et al. |
| 5,564,615 A | 10/1996 | Bishop et al. |
| 5,588,579 A | 12/1996 | Schnut et al. |
| 5,609,285 A | 3/1997 | Grant et al. |
| 5,609,560 A | 3/1997 | Ichikawa et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,865,361 A | 2/1999 | Milliman et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,165,169 A | 12/2000 | Panescu et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 * | 7/2001 | Balazs ................ A61B 17/115 227/175.1 |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |

(56) References Cited

U.S. PATENT DOCUMENTS

| | | |
|---|---|---|
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,240 B2 | 6/2004 | Smith et al. |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,575,144 B2 | 8/2009 | Ortiz et al. |
| 7,585,306 B2 | 9/2009 | Abbott et al. |
| 7,588,174 B2 | 9/2009 | Holsten et al. |
| 7,588,175 B2 | 9/2009 | Timm et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,931 B2 | 5/2010 | Shelton, IV et al. |
| 7,721,932 B2 | 5/2010 | Cole et al. |
| 7,726,539 B2 | 6/2010 | Holsten et al. |
| 7,738,971 B2 | 6/2010 | Swayze et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,803,151 B2 | 9/2010 | Whitman |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |

(56) References Cited

U.S. PATENT DOCUMENTS

| | | | |
|---|---|---|---|
| 7,913,892 B2 | 3/2011 | Cole et al. |
| 7,918,377 B2 | 4/2011 | Fuchs et al. |
| 7,922,061 B2 | 4/2011 | Shelton, IV et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,035,487 B2 | 10/2011 | Malackowski |
| 8,038,046 B2 | 10/2011 | Smith et al. |
| 8,043,207 B2 | 10/2011 | Adams |
| 8,056,787 B2 | 11/2011 | Boudreaux et al. |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky et al. |
| 8,096,458 B2 | 1/2012 | Hessler et al. |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 * | 2/2012 | Milliman ............ A61B 17/068 227/175.1 |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,303,581 B2 | 11/2012 | Arts et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi et al. |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,348,855 B2 | 1/2013 | Hillely et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman et al. |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi |
| 8,453,911 B2 | 6/2013 | Milliman et al. |
| 8,485,414 B2 | 7/2013 | Criscuolo |
| 8,490,853 B2 | 7/2013 | Criscuolo |
| 8,511,533 B2 | 8/2013 | Viola et al. |
| 8,551,138 B2 | 10/2013 | Orban et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,251 B2 | 4/2014 | Rebuffat et al. |
| 8,684,252 B2 | 4/2014 | Patel et al. |
| 8,733,611 B2 | 5/2014 | Milliman |
| 8,752,749 B2 | 6/2014 | Moore et al. |
| 8,758,391 B2 | 6/2014 | Swayze et al. |
| 8,806,973 B2 | 8/2014 | Ross et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2002/0049454 A1 | 4/2002 | Whitman et al. |
| 2002/0165541 A1 | 11/2002 | Whitman |
| 2003/0111507 A1 | 6/2003 | Nunez |
| 2003/0165794 A1 | 9/2003 | Matoba |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0142740 A1 | 6/2006 | Sherman et al. |
| 2006/0201989 A1 | 9/2006 | Ojeda |
| 2007/0023476 A1 | 2/2007 | Whitman et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0167736 A1 | 7/2008 | Swayze et al. |
| 2008/0237296 A1 | 10/2008 | Boudreaux et al. |
| 2008/0308603 A1 | 12/2008 | Shelton et al. |
| 2009/0090763 A1 | 4/2009 | Zemlok et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |

(56) References Cited

U.S. PATENT DOCUMENTS

| | | |
|---|---|---|
| 2010/0163598 A1 | 7/2010 | Belzer |
| 2010/0193568 A1 | 8/2010 | Scheib et al. |
| 2010/0211053 A1 | 8/2010 | Ross et al. |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0006101 A1 | 1/2011 | Hall et al. |
| 2011/0011916 A1 | 1/2011 | Levine |
| 2011/0017801 A1 | 1/2011 | Zemlok et al. |
| 2011/0071508 A1 | 3/2011 | Duval et al. |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0192882 A1 | 8/2011 | Hess et al. |
| 2011/0276057 A1 | 11/2011 | Conlon et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0145766 A1 | 6/2012 | Milliman et al. |
| 2012/0193395 A1 | 8/2012 | Pastorelli et al. |
| 2012/0193398 A1 | 8/2012 | Williams et al. |
| 2012/0223121 A1 | 9/2012 | Viola et al. |
| 2012/0232339 A1 | 9/2012 | Csiky |
| 2012/0245428 A1 | 9/2012 | Smith et al. |
| 2012/0253329 A1 | 10/2012 | Zemlok et al. |
| 2012/0273548 A1 | 11/2012 | Ma et al. |
| 2012/0298719 A1 | 11/2012 | Shelton, IV et al. |
| 2012/0325888 A1 | 12/2012 | Qiao et al. |
| 2012/0330285 A1 | 12/2012 | Hartoumbekis et al. |
| 2013/0015232 A1 | 1/2013 | Smith |
| 2013/0020372 A1 | 1/2013 | Jankowski |
| 2013/0020373 A1 | 1/2013 | Smith et al. |
| 2013/0032628 A1 | 2/2013 | Li |
| 2013/0056516 A1 | 3/2013 | Viola |
| 2013/0060258 A1 | 3/2013 | Giacomantonio |
| 2013/0093149 A1 | 4/2013 | Saur et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Vasudevan et al. |
| 2013/0181035 A1 | 7/2013 | Milliman |
| 2013/0181036 A1 | 7/2013 | Olson et al. |
| 2013/0184704 A1 | 7/2013 | Beardsley et al. |
| 2013/0186930 A1 | 7/2013 | Wenchell |
| 2013/0193185 A1 | 8/2013 | Patel |
| 2013/0193187 A1 | 8/2013 | Milliman |
| 2013/0193190 A1 | 8/2013 | Carter |
| 2013/0193191 A1 | 8/2013 | Stevenson et al. |
| 2013/0193192 A1 | 8/2013 | Casasanta et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman |
| 2013/0240600 A1 | 9/2013 | Bettuchi |
| 2013/0248581 A1 | 9/2013 | Smith et al. |
| 2013/0274722 A1 | 10/2013 | Kostrzewski et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0008413 A1 | 1/2014 | Williams et al. |
| 2014/0012317 A1 | 1/2014 | Orban et al. |
| 2014/0207125 A1 | 7/2014 | Applegate et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1759652 A2 | 3/2007 |
| EP | 1908412 A2 | 4/2008 |
| EP | 1917929 A1 | 5/2008 |
| EP | 1952769 A2 | 8/2008 |
| EP | 2090245 A1 | 8/2009 |
| EP | 2090247 A1 | 8/2009 |
| EP | 2245994 A1 | 11/2010 |
| EP | 2377472 A1 | 10/2011 |
| EP | 2524656 A2 | 11/2012 |
| EP | 2668910 A2 | 12/2013 |
| EP | 2815705 A1 | 12/2014 |
| FR | 1461464 A | 2/1966 |
| FR | 1588250 A | 4/1970 |
| FR | 2443239 A1 | 7/1980 |
| FR | 2861574 A1 | 5/2005 |
| GB | 1185292 A | 3/1970 |
| GB | 2016991 A | 9/1979 |
| GB | 2070499 A | 9/1981 |
| KR | 20120022521 A | 3/2012 |
| NL | 7711347 A | 4/1979 |
| SU | 1509052 A1 | 9/1989 |
| WO | WO 8706448 A | 11/1987 |
| WO | WO 8900406 A1 | 1/1989 |
| WO | WO 9006085 A1 | 6/1990 |

(56) References Cited

FOREIGN PATENT DOCUMENTS

WO     WO 01-54594 A1      8/2001
WO     WO 2008-107918 A1   9/2008

OTHER PUBLICATIONS

Partial European Search Report corresponding to European Appln. No. EP 15166899 dated Oct. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, mailed Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
European Search Report dated Apr. 4, 2017, issued in EP Application No. 16200219.
European Examination Report dated Mar. 30, 2017, issued in EP Application No. 15166899.

* cited by examiner

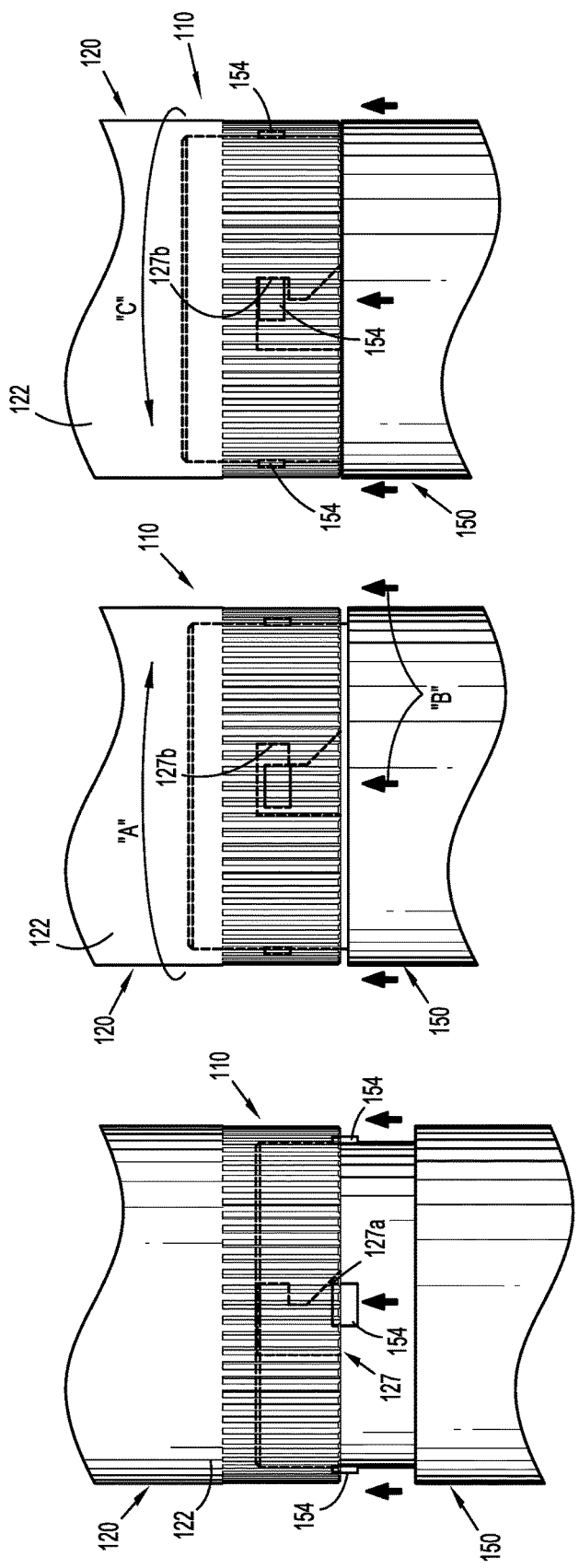

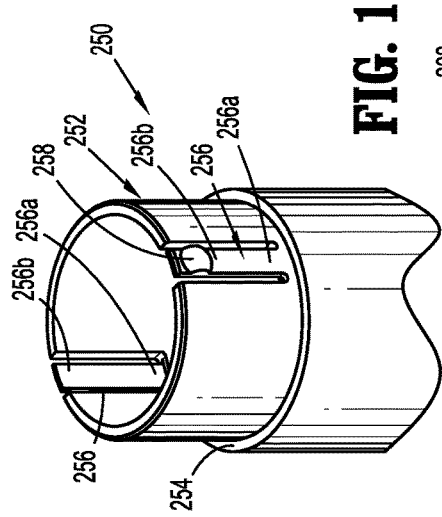
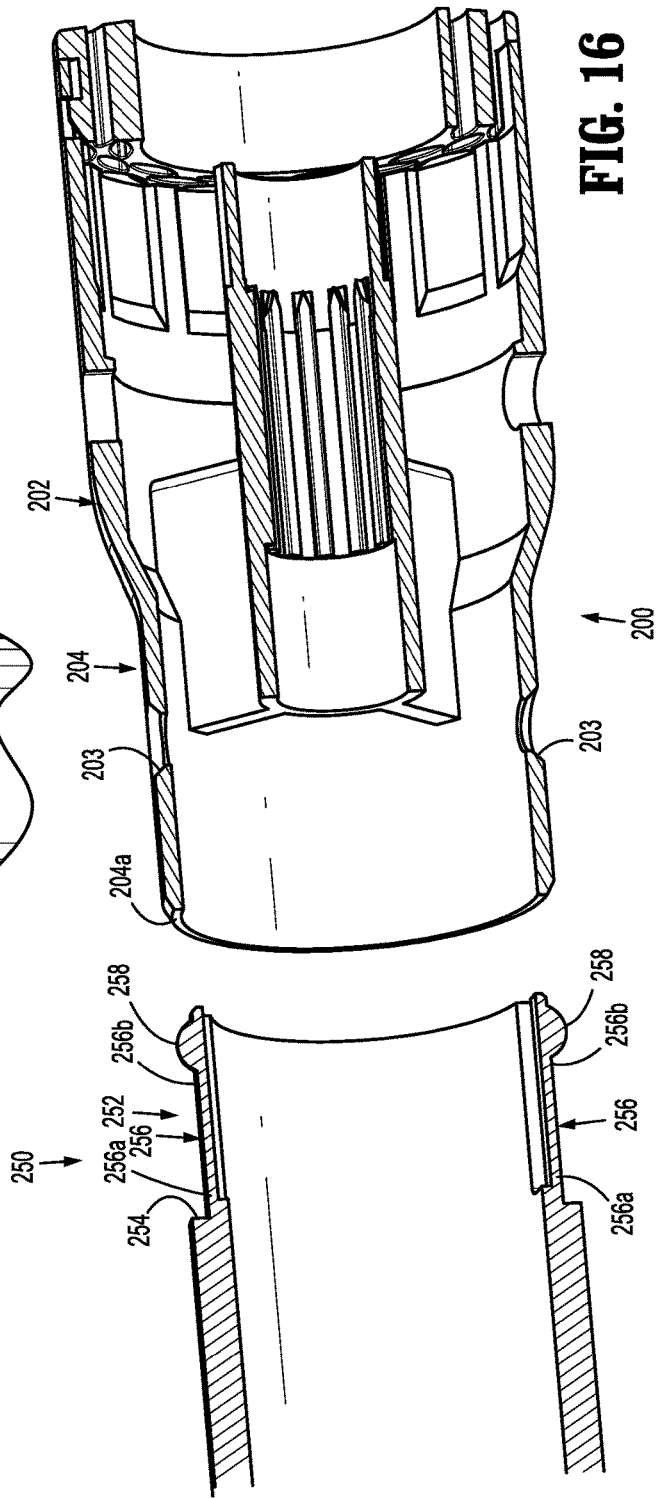

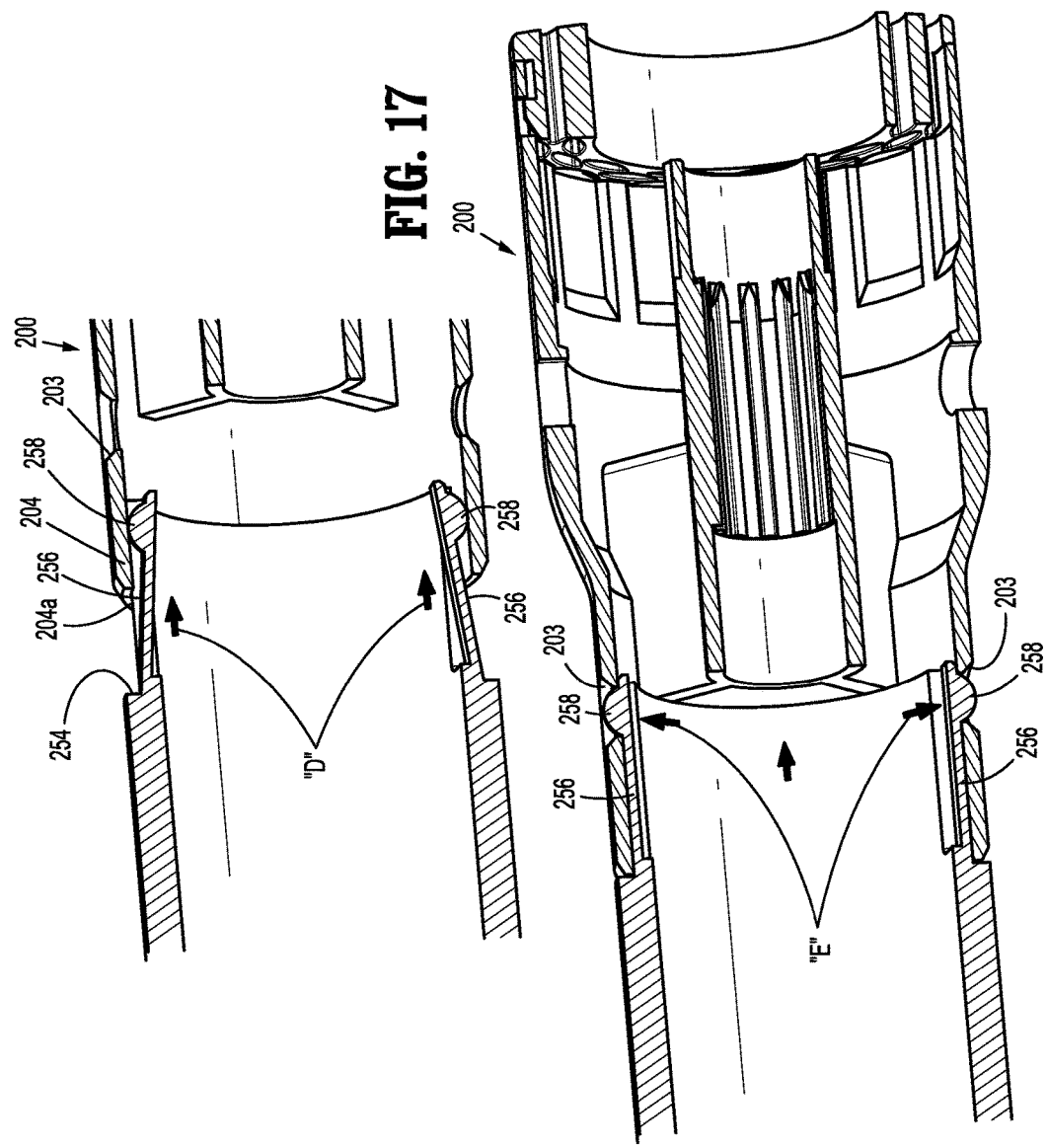

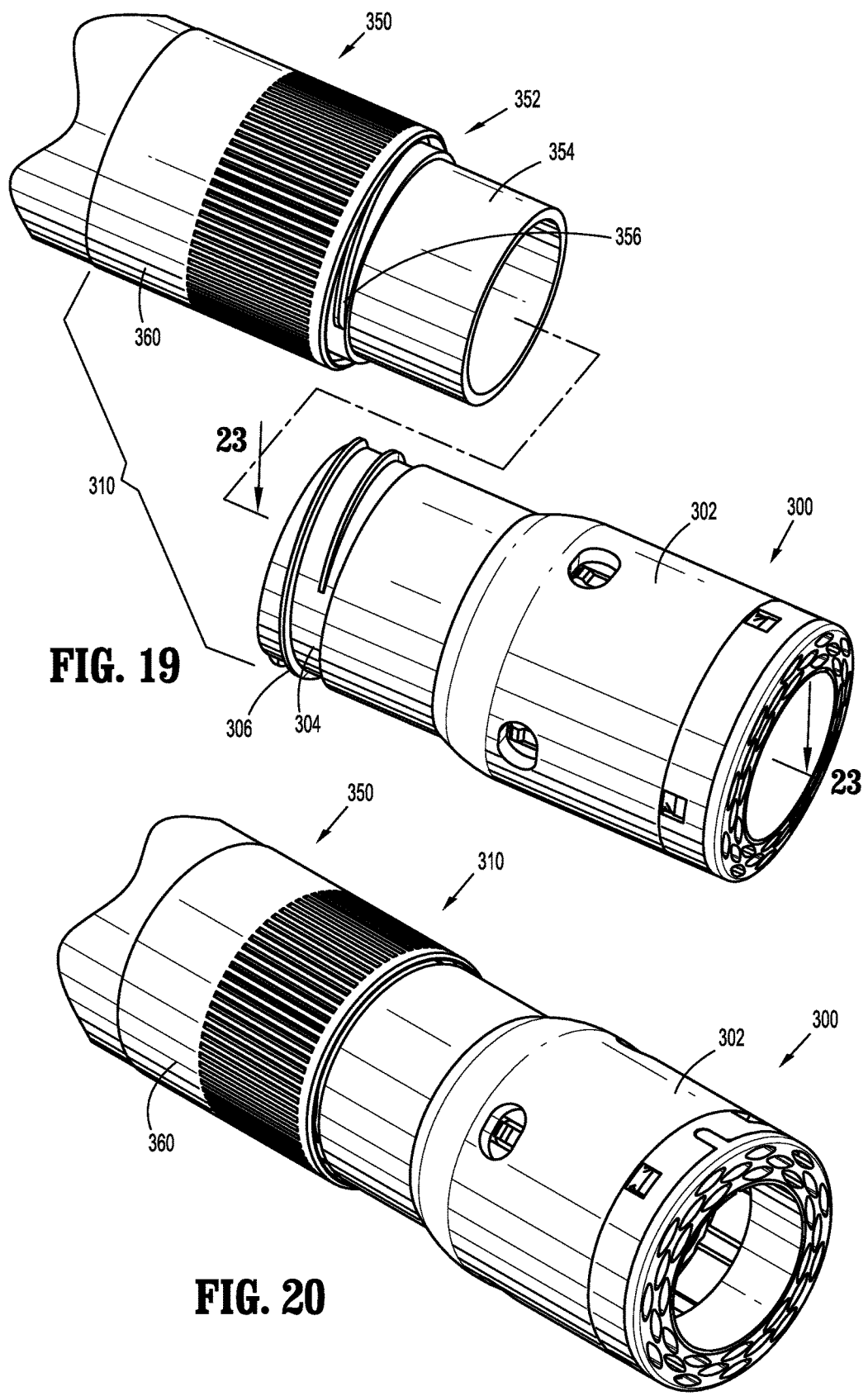

INTERLOCK ASSEMBLIES FOR REPLACEABLE LOADING UNIT

BACKGROUND

Technical Field

The present disclosure relates to surgical stapling devices including replaceable loading units. More particularly, the present disclosure relates to interlock assemblies for operably securing the replaceable loading units to an actuation assembly of the surgical stapling device and/or surgical adapter assembly.

Background of Related Art

Surgical devices for applying staples, clips, or other fasteners to tissue are well known. Endoscopic stapling devices include an actuation unit, i.e., a handle assembly for actuating the device and a shaft for endoscopic access, and a tool assembly disposed at a distal end of the shaft. Certain of these devices are designed for use with a replaceable loading unit which includes the tool assembly and houses the staples or fasteners. The replaceable loading unit may include staples of various sizes and the staples may be arranged in one or more configurations. After firing the stapling device with a replaceable loading unit, the user may detach the empty replaceable loading unit from the actuation unit, select and attach a second replaceable loading unit to the actuation unit, and fire the stapling device again. This process may be performed repeatedly during a surgical procedure.

Many of the stapling devices include an interlock assembly for selectively attaching the replaceable loading units to the actuation unit. The components of the interlock assemblies are typically located on the elongated bodies of the actuation unit or on adapter assemblies connected to the actuation unit. The sterilization and cleaning of the actuation units and adapter assemblies are complicated because of the location of the interlocking components on the elongated bodies or adapter assemblies.

Therefore, it would be beneficial to have a surgical device in which the components of the interlock assemblies are located on the loading units and, thus do not require sterilization.

SUMMARY

Accordingly, an interlock assembly for attaching a loading unit to a surgical stapling instrument is provided. The interlock assembly includes a shell member, a collar member, and an adapter assembly. The shell member has a proximal end including a first cylindrical portion and a second cylindrical portion and a distal end supporting a staple cartridge defining a plurality of staple retaining slots arranged in a pair of concentric rows. The collar member is received about the first and second cylindrical portion and is moveable between a locked position and an unlocked position. The collar member defines a plurality of slots. The adapter assembly includes a distal end selectively securable to the proximal end of the shell member. The adapter assembly includes a plurality of lugs selectively receivable within the plurality of slots when the collar member is in the unlocked position and secured within the slots when the collar member is in the locked position.

The interlock assembly may further including a torsion spring operably received about the first cylindrical portion for biasing the collar member to the locked position. In one embodiment, the distal end of the adapter assembly is receivable about the first cylindrical portion of the shell member. The first cylindrical portion may include a pair of tabs configured for receipt within a pair of longitudinal slots defined by the distal end of the adapter assembly. The collar member may include an outer surface configured to facilitate operable engagement by a user.

Another interlock assembly for attaching a loading unit to a surgical stapling instrument is provided. The interlock assembly includes a shell member and an adapter assembly. The shell member has a proximal end defining a pair of openings and a distal end supporting a staple cartridge defining a plurality of staple retaining slots arranged in a pair of concentric rows. The adapter assembly includes a distal end securable to the proximal end of the shell member, the adapter assembly including a pair of arms each including a protrusion of a free end thereof, wherein each of the protrusions are received within the pair of openings when the distal end of the adapter assembly is received within the proximal end of the shell member. The distal end of the adapter assembly may define a ledge configured to engage a proximal surface of the proximal end of the shell member when the distal end of the adapter assembly is received within the proximal end of the shell member to facilitate alignment of the pair of protrusions with the pair of openings. The pair of arms may be flexible radially inward.

Still another interlock assembly for attaching a loading unit to a surgical stapling instrument is provided. The interlock assembly includes a shell member having a proximal end that includes a first threaded portion and a distal end that supports a staple cartridge defining a plurality of staple retaining slots arranged in a pair of concentric rows. The interlock assembly further includes an adapter assembly that includes a distal end having a flange receivable within the proximal end of the shell member and a second threaded portion disposed proximal of the flange. The interlock assembly also includes a collar member received about the distal end of the adapter assembly and includes an internally threaded portion in engagement with the second threaded portion. The collar member may be moveable into selective engagement with the first threaded portion when the flange of the adapter assembly is received within the proximal end of the shell member. The collar member may include an outer surface configured to facilitate selective engagement by a user.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 9 is a side view of the interlock assembly of the replaceable loading unit and adapter assembly shown in FIG. 1 prior to receipt of a lug of the adapter assembly within a bayonet-type slot of the loading unit;

FIG. 10 is a side view of the interlock assembly of FIG. 1 upon receipt of the lug of the adapter assembly within the slot of the loading unit;

FIG. 11 is a side view of the interlock assembly of FIGS. 9 and 10 with the lug of the adapter assembly secured within the slot of the replaceable loading unit;

FIG. 15 is a perspective view of the distal end of the adapter assembly shown in FIG. 13;

FIG. 16 is a cross-sectional perspective view of the replaceable loading unit shown in FIG. 13, with internal components removed, and a cross-sectional perspective view of the distal end of the adapter assembly shown in FIG. 13;

FIG. 17 is a cross-sectional perspective view of a proximal end of the replaceable loading unit and distal end of the adapter assembly shown in FIG. 16, with the replaceable loading unit partially attached to the adapter assembly;

FIG. 18 is a cross-sectional perspective view of the replaceable loading unit and distal end of the adapter assembly shown in FIG. 16, with the replaceable loading unit attached to the adapter assembly;

FIG. 19 is a perspective view of a replaceable loading unit, according to another embodiment of the present disclosure, and a distal end of an adapter assembly, according to another embodiment of the present disclosure;

FIG. 20 is a perspective view of the replaceable loading unit shown in FIG. 19 attached to the adapter assembly shown in FIG. 19;

DETAILED DESCRIPTION

Figure 1:
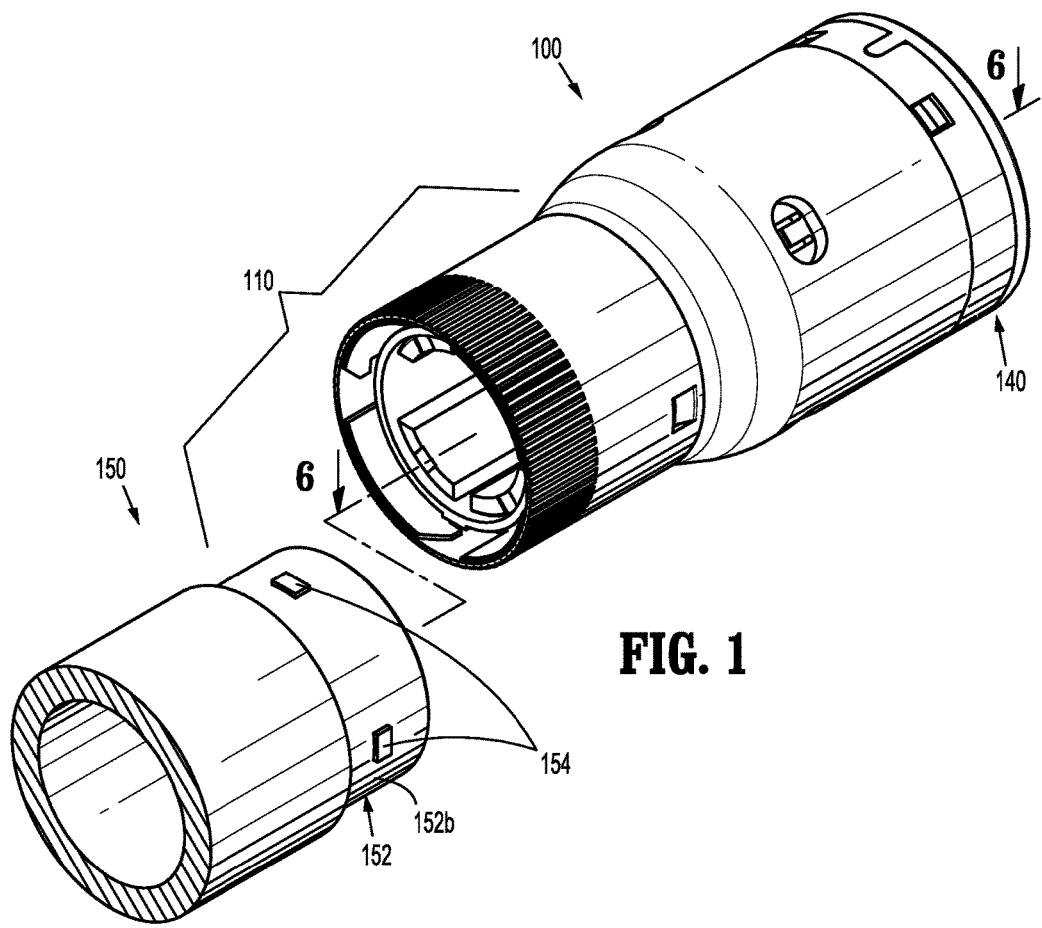
FIG. 1 is a perspective view of a replaceable loading unit, according to an embodiment of the present disclosure, and a distal end of an adapter assembly, according to an embodiment of the present disclosure.

Embodiments of the presently disclosed interlock assemblies will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Figure 2:
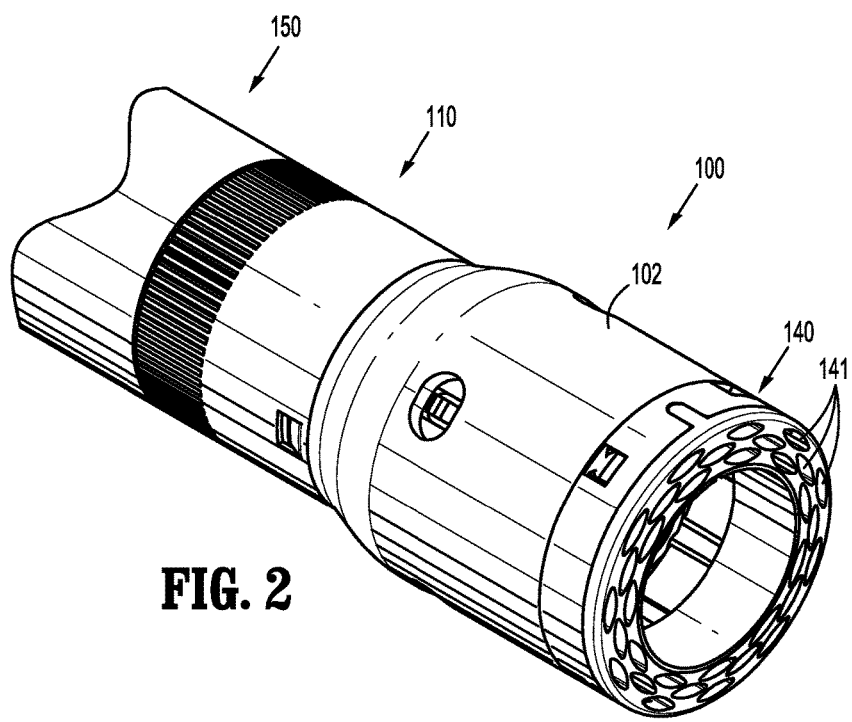
FIG. 2 is a perspective view of the loading unit shown in FIG. 1 selectively attached to the distal end of the adapter assembly shown in FIG. 1.

With reference to FIGS. 1 and 2, an interlock assembly, according to an embodiment of the present disclosure, is shown generally as interlock assembly 110. Interlock assembly 110 is formed on a proximal end 104 of a loading unit 100 and a distal end 152 of an adapter assembly 150. Interlock assembly 110 is configured to operably secure loading unit 100 to adapter assembly 150. Adapter assembly 150 is configured to operably connect loading unit 100 to a surgical stapling device (not shown). Although interlock assembly 110 will be shown and described with reference to loading unit 100 and adapter assembly 150, it is envisioned that interlock assembly 110 may be modified for use on different loading units and with different adapter assemblies. Alternatively, interlock assembly 110 may be modified to be connected directly to an elongate body (not shown) of an actuation assembly (not shown). Loading unit 100 and adapter assembly 150 will only be described to the extent necessary to fully disclose the aspects of the present disclosure.

For a more detailed description of exemplary loading units and adapter assemblies, please refer to commonly owned U.S. Patent Application Publication No. 2013/0181035, the content of which is incorporated by reference herein in its entirety. Exemplary electromechanical surgical stapling devices for operating adapter assembly and/or loading units are shown and described in U.S. Patent Application Publication No 2012/0253329, the content of which is also incorporated by reference herein in its entirety.

Figure 3:
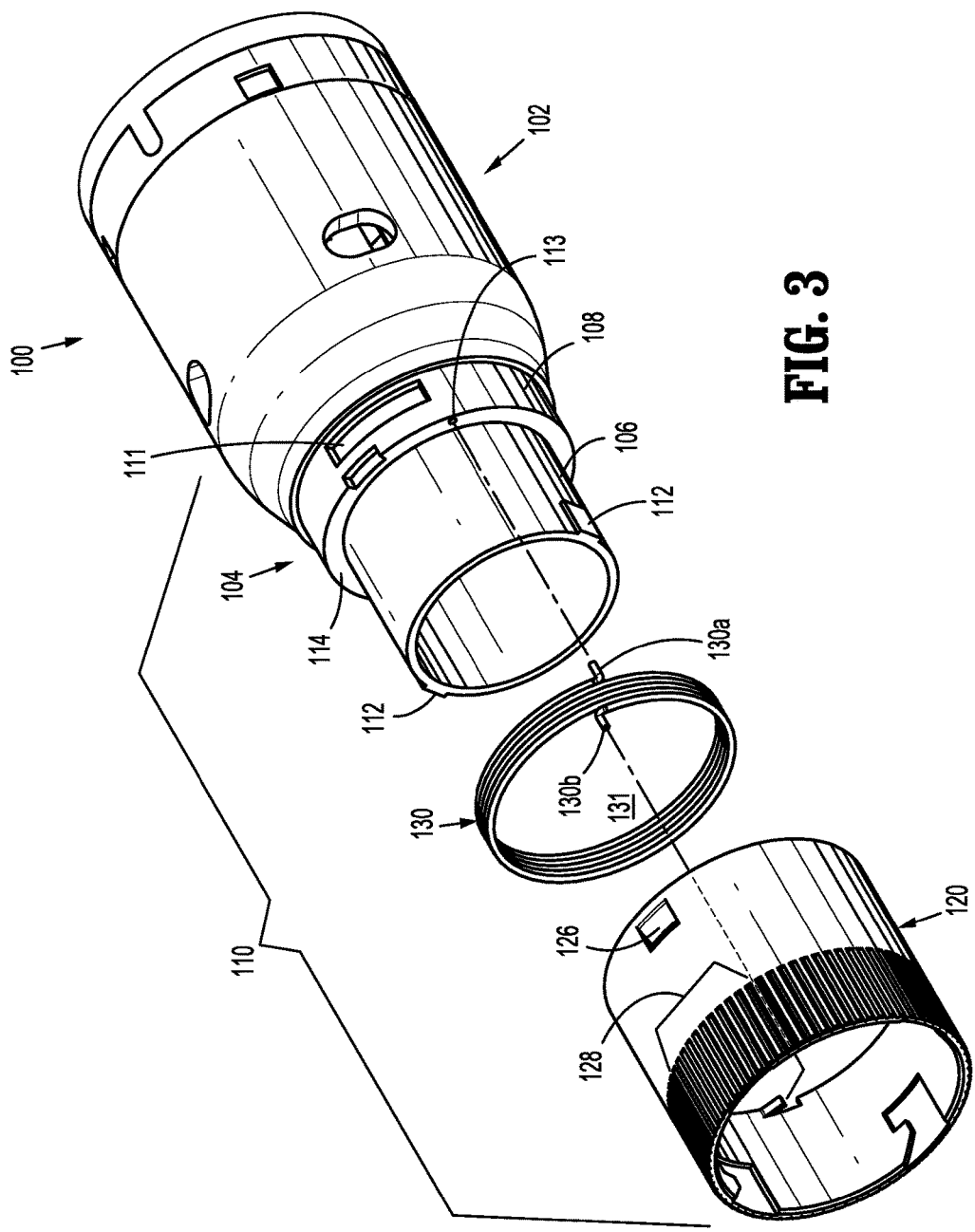
FIG. 3 is an exploded perspective view of the replaceable loading unit shown in FIG. 1.
Figure 4:
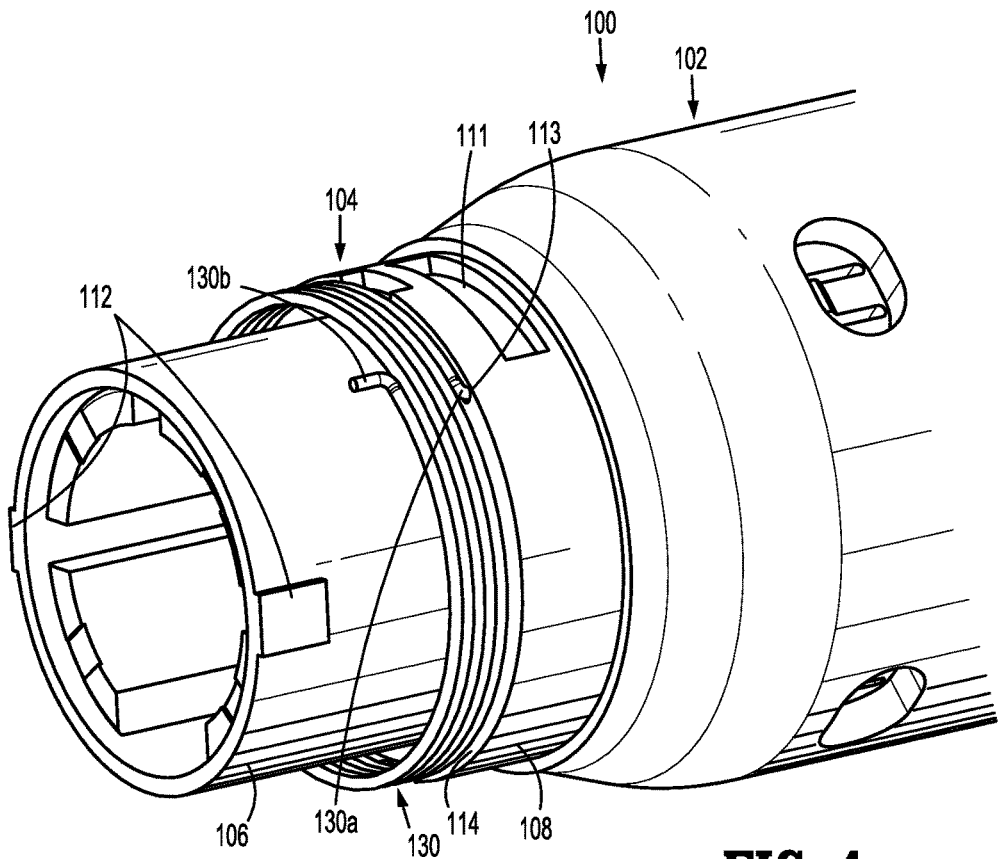
FIG. 4 is a perspective view of the proximal end of the replaceable loading unit shown in FIG. 1 with a collar member removed.

With reference now to FIGS. 3 and 4, loading unit 100 includes a shell member 102. Interlock assembly 110 is located on a proximal end 104a of shell member 102 and includes a first cylindrical portion 106 and a second cylindrical portion 108, a collar member 120, and a torsion spring 130. First cylindrical portion 106 of interlock assembly 110 is configured to be received within a longitudinal opening 151 (FIG. 8) of adapter assembly 150. A pair of lugs 112 extend radially outward from first cylindrical portion 106 and are configured to be received within slots 153 (FIG. 8) formed on an inner surface 152a of distal end 152 of adapter assembly 150. Second cylindrical portion 108 of interlock assembly 110 is configured to be received within collar member 120 of interlock assembly 110. Second cylindrical portion 108 of interlock assembly 110 defines a pair of notches 111 (FIG. 12) each configured to receive a tab 126 formed on and extending radially inward from a distal portion 124 of collar member 120. As will be described in further detail below, receipt of tabs 126 within notches 111 of second cylindrical portion 108 limits the amount of rotation between collar member 120 and shell member 102. A ledge 114 is formed between first cylindrical portion 106 and second cylindrical portion 108. Ledge 114 defines a hole or aperture 113 configured to receive a first end 130a of torsion spring 130 of interlock assembly 110.

A distal end 104b of shell member 102 supports a staple cartridge 140 (FIG. 2). Staple cartridge 140 may be releasable secured to shell member 102 to permit replacement of staple cartridge 140 after firing. Staple cartridge 140 defines a plurality of staple retaining slots 141 arranged in a pair of concentric rows and is configured to retain a plurality of staples (not shown).

Figure 5:
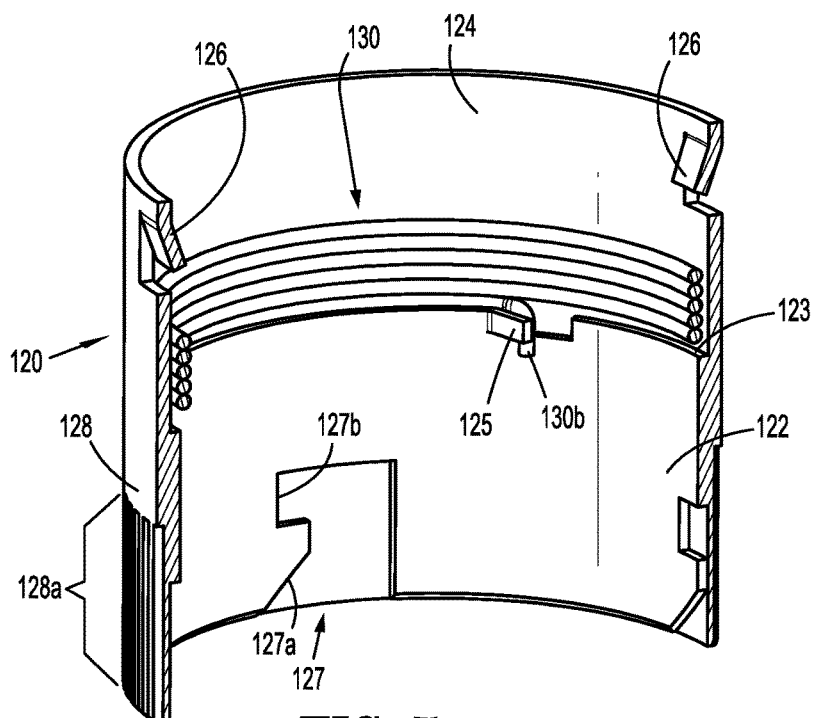
FIG. 5 is a cross-sectional perspective view of a collar member of the replaceable loading unit shown in FIG. 1.

With particular reference now to FIG. 5, collar member 120 forms a cylindrical member configured to be rotatably received about proximal end 104 of shell member 102. Collar member 120 includes a proximal portion 122 and a distal portion 124. Proximal and distal portions 122, 124 are separated by a ledge 123. Distal portion 124 of collar member 120 is dimensioned to be received within an opening 131 of torsion spring 130 and ledge 123 is configured to retain torsion spring 130 within collar member 120. Collar member 120 includes a flap 125 configured to engage a second end 130b of torsion spring 130. As noted above, distal portion 124 of collar member 120 includes a pair of tabs 126 configured to be received within notches 111 (FIG. 12) of second cylindrical portion 108 of interlock assembly 110 and are configured to limit the rotational movement of collar member 120 relative to shell member 102.

Still referring to FIG. 5, proximal portion 122 of collar member 120 defines a plurality of bayonet-type slots 127 for selectively engaging lugs 154 that extend radially outward from adapter assembly 150. Slots 127 are defined by a slanted or angled portion 127a of proximal portion 122 of collar member 120 and a recessed portion 127b of proximal portion 124a of collar member 120. As will be described in further detail below, slanted portions 127a of collar member 120 are configured to direct lugs 154 of adapter assembly 150 within slots 127 of collar member 120 and recessed portions 127b of collar member 120 are configured to selectively maintain lugs 154 (FIG. 8) of adapter assembly 150 within slots 127 of collar member 120. Accordingly, slots 127 in collar member 120 correspond in size and location to lugs 154 formed on adapter assembly 150.

As shown, proximal portion 124 of collar member 120 includes four (4) slots 127, however, collar member 120 may include any number of slots 127. It is envisioned that the number of slots 127 may be more then the number of lugs 154 formed on adapter assembly 150. An outer surface 128 of proximal portion 124 may include ridges 128a or otherwise be configured to facilitate operable engagement by a user.

Figure 6:
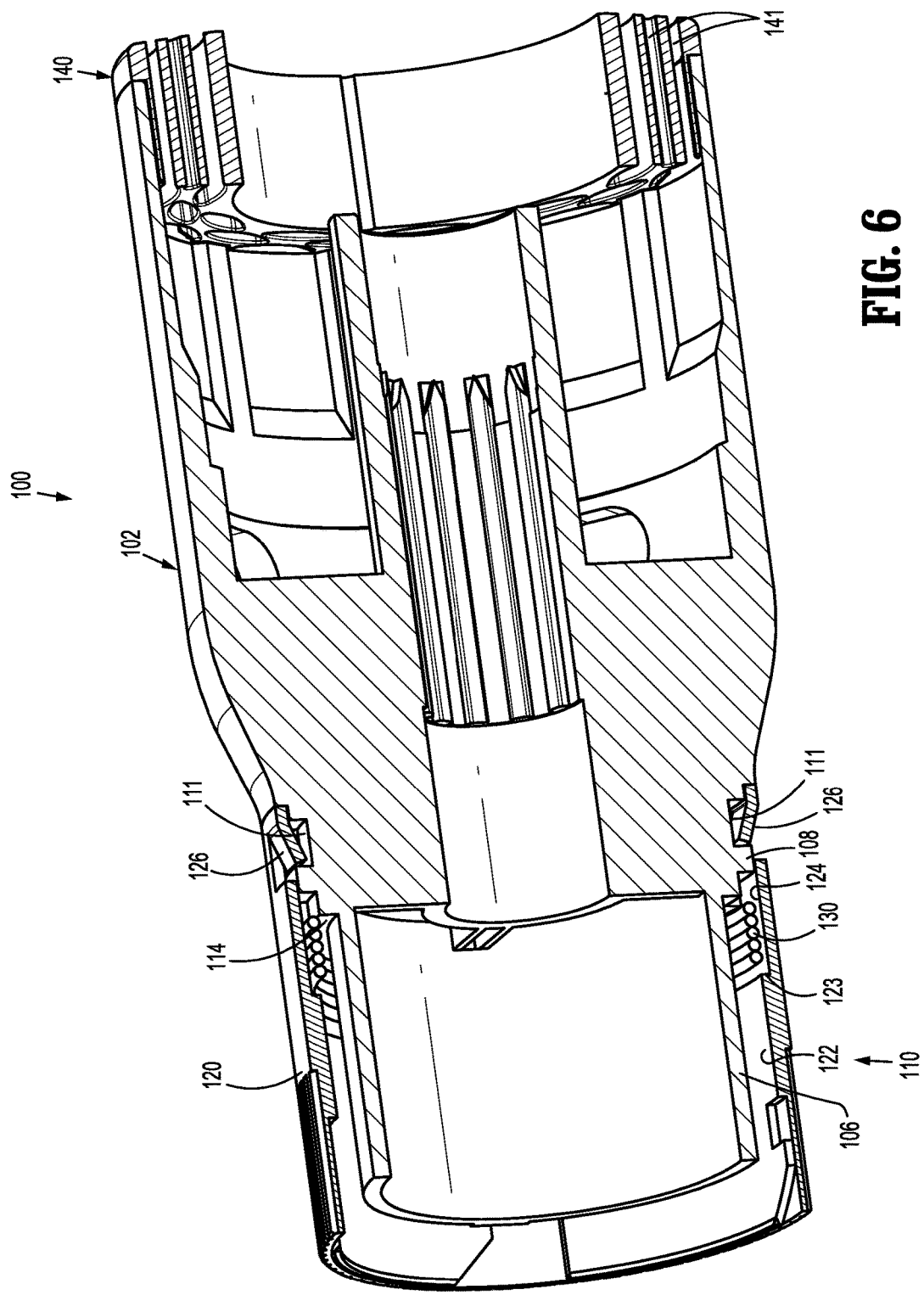
FIG. 6 is a cross-sectional perspective side view of the loading unit shown in FIG. 1 with internal components removed.

Turning now to FIG. 6, collar member 120 is shown rotatably received about proximal end 104 of shell member 102. Tabs 126 of collar member 120 are positioned within notches 111 of second cylindrical portion 108 of interlock assembly 110 to limit the rotation of collar member 120 relative to shell member 102.

Torsion spring 130 is received between ledge 114 formed between first and second cylindrical portions 106, 108 and ledge 123 formed between proximal and distal portions 122, 124 of collar member 120. First end 130a (FIG. 4) of torsion spring 130 is received within hole 113 formed in ledge 112 of shell member 102 (FIG. 4) and second end 130b (FIG. 5) of torsion spring 130 engages flap 123a of collar member 120. As will be described in further detail below, torsion spring 130 maintains an angular position/orientation of collar member 120 relative to shell member 102.

Figure 7:
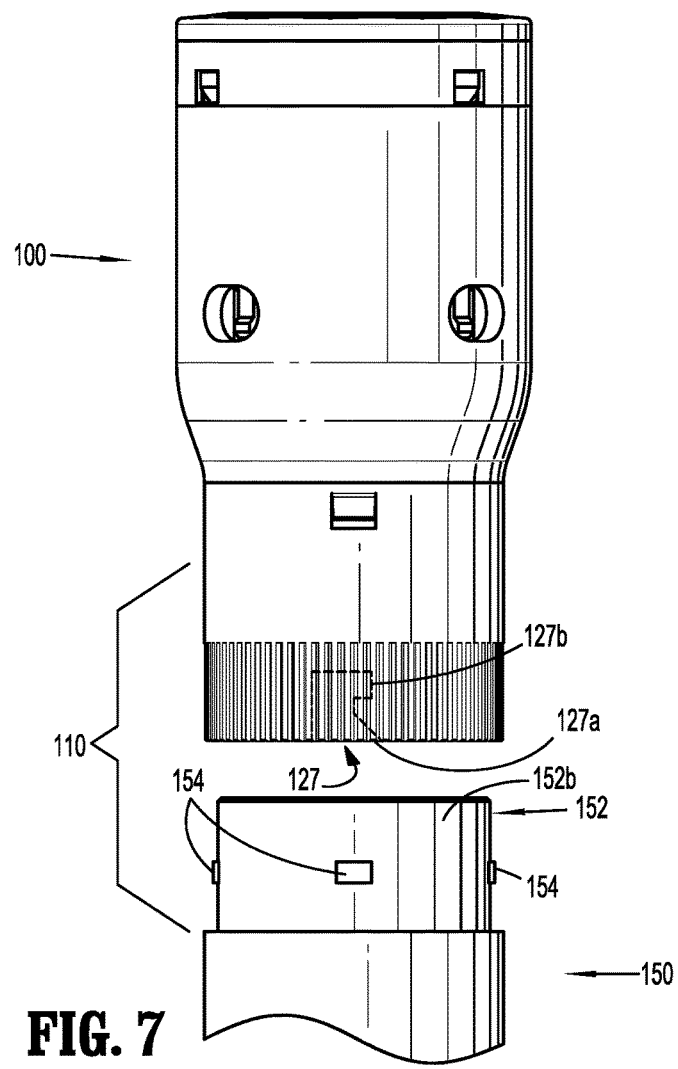
FIG. 7 is a side view of the replaceable loading unit shown in FIG. 1 and the distal end of the adapter assembly shown in FIG. 1, prior to attachment of the loading unit to the adapter assembly.
Figure 8:
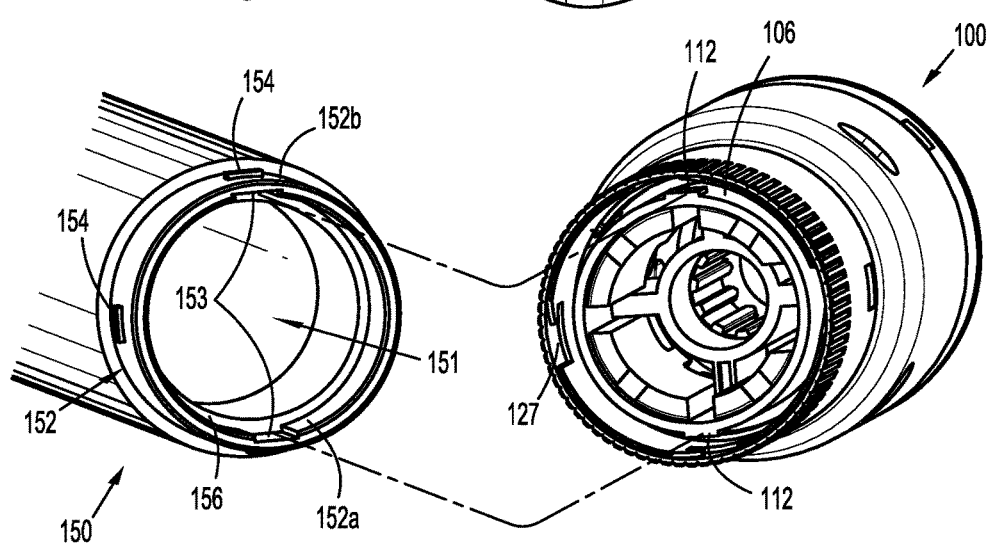
FIG. 8 is a perspective end view of the distal end of the adapter assembly shown in FIG. 1 and a perspective view of the proximal end of the replaceable loading unit shown in FIG. 1.

With reference now to FIGS. 7 and 8, adapter assembly 150 is operably connected to an actuation unit (not shown) for actuating replaceable loading unit 100. Slots 153 (FIG. 8) are defined on an internal surface 152a of a distal end 152 of adapter assembly 150 and lugs 154 are formed on an outer surface 152b of distal end 152 of adapter assembly 150. As noted above, slots 153 of adapter assembly 150 are configured to receive lugs 112 formed on first cylindrical portion 106 of interlock assembly 110 and lugs 154 of adapter assembly 150 are configured to be received within slots 127 of collar member 120 of interlock assembly 110. Distal end 152 of adapter assembly 150 may further include a shelf 156. As will be described in further detail below, shelf 156 is configured to engage a proximal end 106a of first cylindrical portion 106 of interlock assembly 110 when loading unit 100 is received about distal end 152 of adapter assembly 150.

The operation of interlock assembly 110 will now be described with reference to FIGS. 7-11. With continued reference to FIGS. 7 and 8, loading unit 100 is aligned and/or oriented relative to adapter assembly 150 such that lugs 154 (FIG. 8) on first cylindrical portion 106 of interlock assembly 110 align with slots 153 (FIG. 8) of adapter assembly 150. Turning to FIG. 9, as loading unit 100 is longitudinally advanced over adapter assembly 150, lugs 154 formed on adapter assembly 150 are received within slots 127 formed in proximal portion 122 of collar member 120. In particular, lugs 154 of adapter assembly 150 engage slanted portions 127a of proximal portion 122 of collar member 120. Engagement of lugs 154 with slanted portions 127a results in rotation of collar member 120, as indicated by arrow "A" (FIG. 10), in a clockwise direction relative to adapter assembly 150.

Rotation of collar member 120 in the clockwise direction, as shown, permits further advancement of loading unit 100 relative to adapter assembly 150, as indicated by arrows "B". As collar member 120 is rotated in the clockwise direction, torsion spring 130 is expanded (radially), recreating a spring bias against collar member 120 in the counter-clockwise direction. As loading unit 100 is fully advanced over adapter assembly 150, lugs 154 of adapter assembly 150 are fully received within slots 127.

Turning to FIG. 11, once lugs 154 of adapter assembly 150 are fully received within slots 127 of collar member 120, lugs 154 of adapter assembly 150 align with recessed portion 127b of proximal portion 122 of collar member 120. The spring bias of torsion spring 130 (FIG. 12), acting on collar member 120, causes collar member 120 to rotate in a counter-clockwise direction, as indicated by arrow "C" in FIG. 11, returning collar member 120 to a pre-rotated position. Rotation of collar member 120 in the counter-clockwise direction, i.e., return of collar member 120 to the pre-rotated position, positions recessed portion 127b of proximal portion 122 of collar member 120 about lugs 154 of adapter assembly 150, thereby securing loading unit 100 relative to adapter assembly 150.

Figure 12:
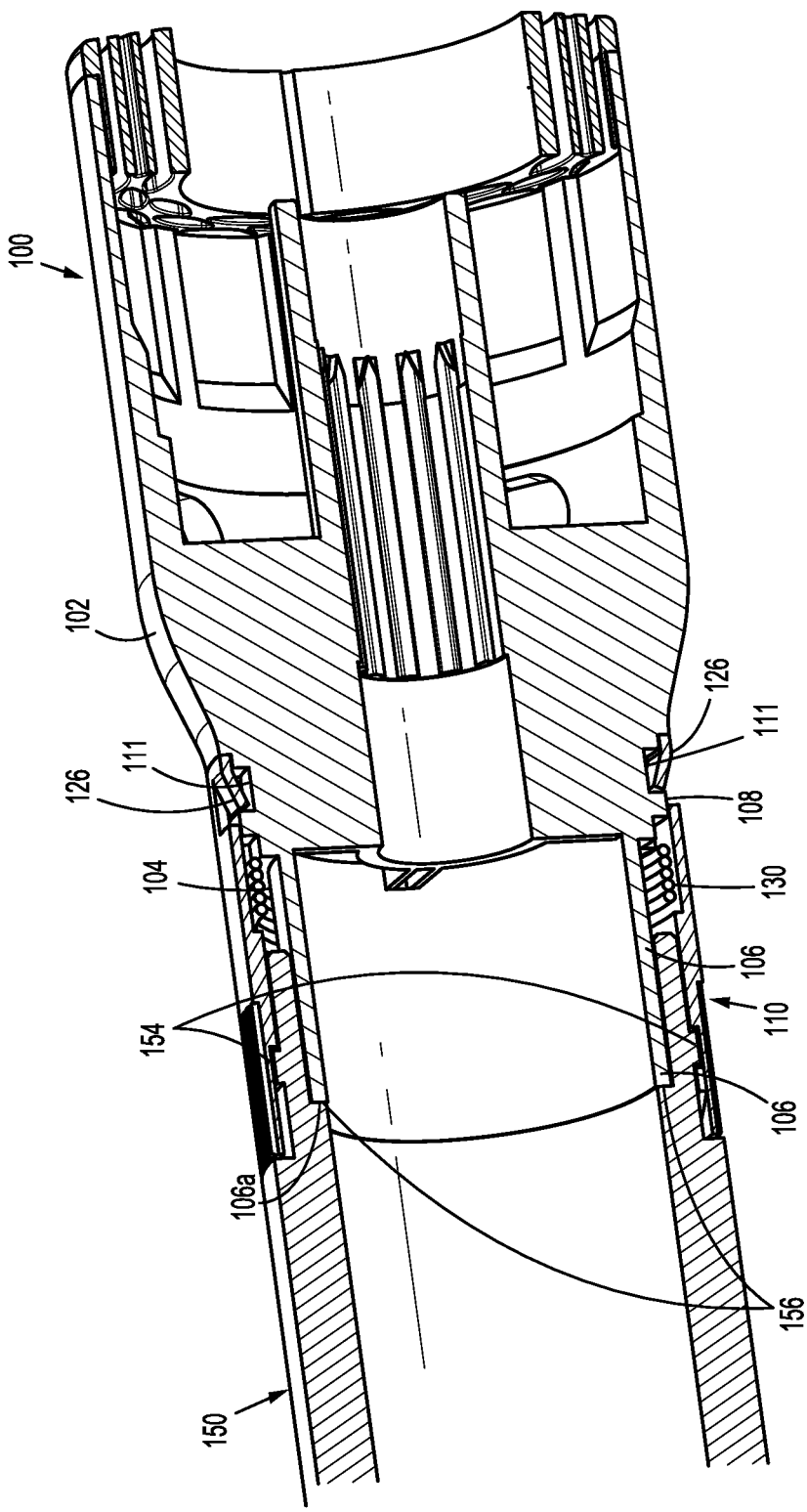
FIG. 12 is a cross-sectional perspective view of the replaceable loading unit and distal end of the adapter assembly shown in FIG. 1 with the replaceable loading unit securely attached to the adapter assembly.
Figure 13:
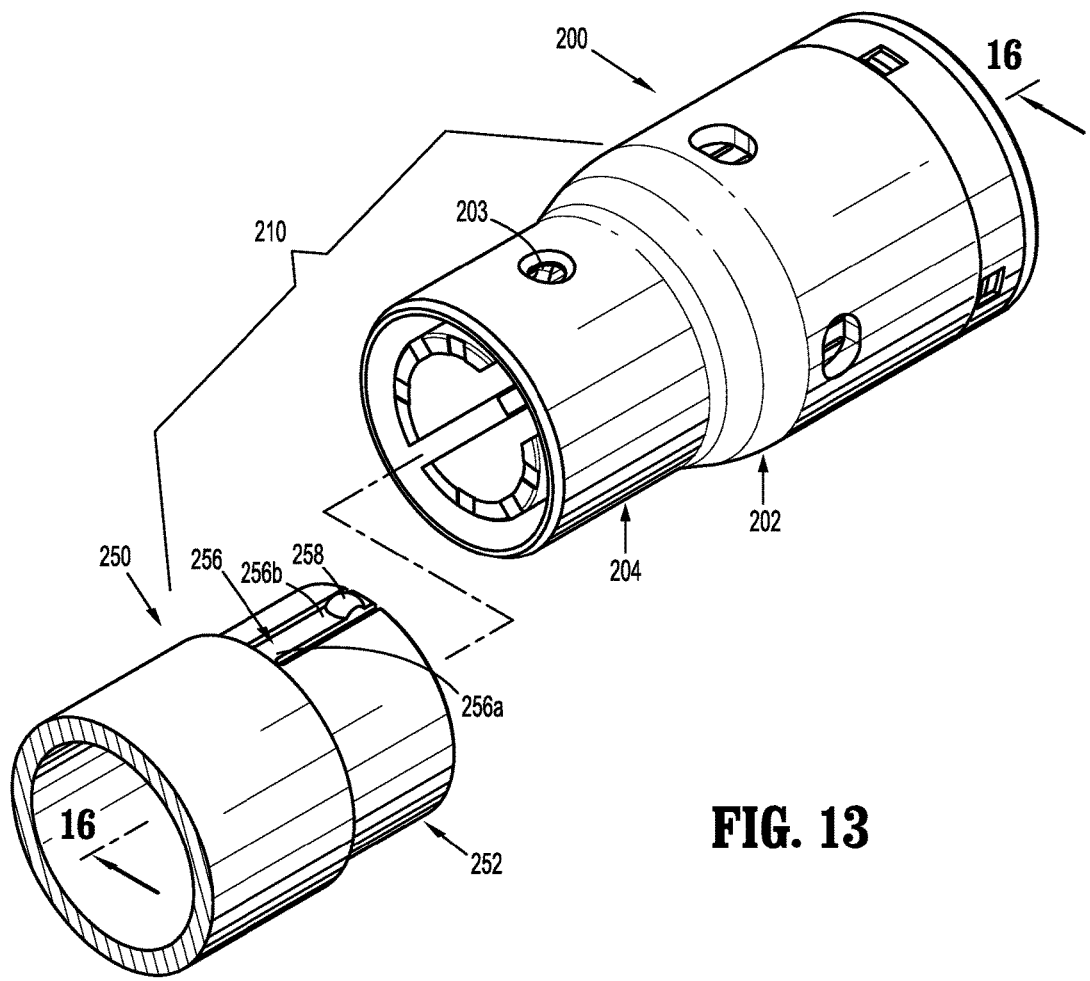
FIG. 13 is a perspective view of a replaceable loading unit, according to another embodiment of the present disclosure, and a distal end of an adapter assembly, according to another embodiment of the present disclosure.
Figure 14:
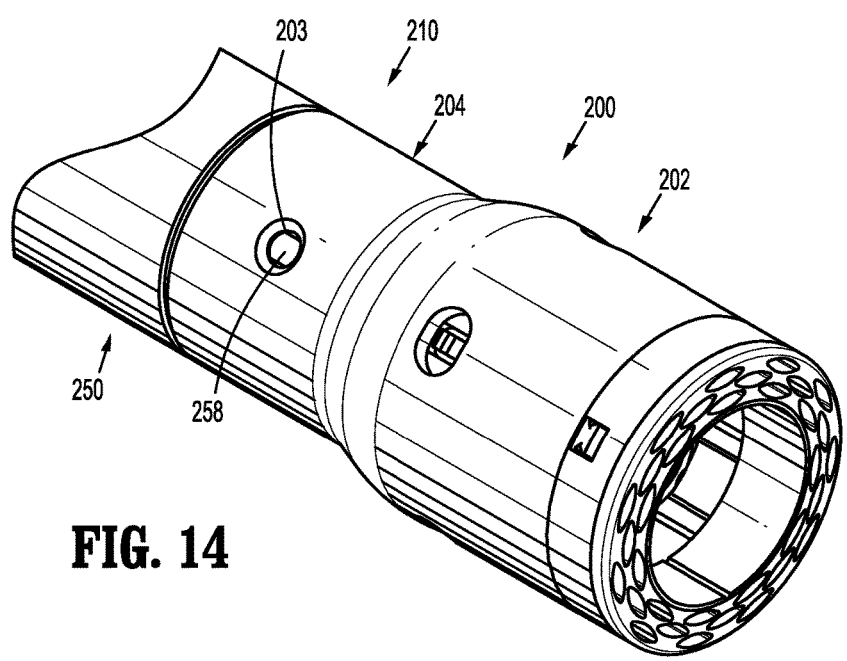
FIG. 14 is a perspective view of the replaceable loading unit shown in FIG. 13 selectively attached to the distal end of the adapter assembly shown in FIG. 13.

With reference to FIG. 12, when loading unit 100 is secured to adapter assembly 150, lugs 154 of adapter assembly 150 are securely received within slots 127 of collar member 120 and the proximal end 106a of first cylindrical portion 106 of interlock assembly 110 engages shelf 156 of adapter assembly 150.

Loading unit 100 may be disconnected from adapter assembly 150 in the opposite manner of connection. Specifically, collar member 120 of interlock assembly 110 may be rotated in the clockwise direction to remove lugs 154 of adapter assembly 150 from within recessed portions 127b of collar member 120, and loading unit 100 may be retracted longitudinally relative to adapter assembly 150 to withdraw loading unit 100 from about distal end 152 of adapter assembly 150. Second or subsequent loading units 100 may then be attached to adapter assembly 150 in the manner prescribed above.

With reference now to FIGS. 13-18, an interlock assembly, according to another embodiment of the present disclosure, is shown generally as interlock assembly 210. Interlock assembly 210 is formed on a proximal end 204 of a loading unit 200 and a distal end 252 of an adapter assembly 250. Interlock assembly 210 is configured to operably secure loading unit 200 to adapter assembly 250.

With reference to FIGS. 13-16, loading unit 200 is substantially similar to loading unit 100 described hereinabove, and will only be described to the extent necessary to identify the differences therebetween. Loading unit 200 includes a shell member 202 having a proximal end 204 configured to be received about distal end 252 of adapter assembly 250. Proximal end 204 of shell member 202 defines a pair of openings 203. As will be described in further detail below, openings 203 are configured to receive protrusions 258 formed on free ends 256b of legs 256 formed on distal end 252 of adapter assembly 250.

With reference still to FIGS. 13-16, adapter assembly 250 includes distal end 252 configured to be received within proximal end 204 of shell member 202 and a shelf 254 configured to engage a proximal surface 204a of proximal end 204 of shell member 202. Distal end 254 includes legs 256 flexibly attached at a first end 256a thereof. As noted above, protrusions 258 are formed on free end 256b of each of leg 256.

The operation of interlock assembly 210 will now be shown and described with reference to FIGS. 17 and 18. Referring initially to FIG. 17, distal end 252 of adapter assembly 250 is aligned with proximal end 204 of shell member 202 of loading unit 200. Advancement of adapter assembly 250 relative to loading unit 200, as indicated by arrows "D" in FIG. 18, causes legs 256 on distal end 252 of adapter assembly 250 to flex radially inward thereby permitting continued advancement of adapter assembly 250 relative to shell member 202 of loading unit 200.

Turning now to FIG. 18, engagement of proximal surface 204a of proximal end 204 of shell member 202 of loading unit 200 with shelf 254 of adapter assembly 250 aligns protrusions 258 on free ends 256b of legs 256 of adapter assembly 250 to align with openings 203 formed in proximal end 204 of shell member 202 of loading unit 200. Alignment of protrusions 258 with openings 203 permits free ends 256b of legs 256 to return to an unflexed condition, as indicated by arrows "E" in FIG. 18, in which protrusions 258 of adapter assembly 250 are received within openings 203 of shell member 202 of loading unit 200. Receipt of protrusions 258 on legs 256 of adapter assembly 250 with openings 203 in shell member 202 of loading unit 200 secures loading unit 200 to adapter assembly 250. It is envisioned that one of proximal end 204 of shell member 202 and distal end 252 of adapter assembly 250 may include one or more longitudinal tabs or slots (not shown) and the other of proximal end 204 of shell member 202 and distal end 252 of adapter assembly 250 may include one or more corresponding slots or tabs (not shown) to facilitate alignment of protrusions 258 on legs 256 of adapter assembly 250 with openings 203 in shell member 202 of loading unit 200.

Loading unit 200 is separated from adapter assembly 250 in the opposite manner of attachment. Specifically, protrusions 258 on legs 256 of adapter assembly 250 are depressed radially inward to cause legs 256 to flex such that protrusions 258 are pushed from within openings 203 in shell member 202 of loading unit 200. Once protrusions 258 of legs 256 no longer reside within openings 203 of shell member 202 of loading unit 200, adapter assembly 250 may be longitudinally retracted relative to loading unit 200 to cause the separation of loading unit 200 from adapter assembly 250. One or more subsequent loading units 200 may be attached to and removed from adapter assembly 250 in the manner described above.

With reference now to FIGS. 19-25, an interlock assembly, according to another embodiment of the present disclosure, is shown generally as interlock assembly 310. Interlock assembly 310 is formed on a proximal end 304 of a loading unit 300, a distal end 352 of an adapter assembly 350, and includes a collar member 360. Interlock assembly 310 is configured to operably secure loading unit 300 to adapter assembly 350.

Figure 21:
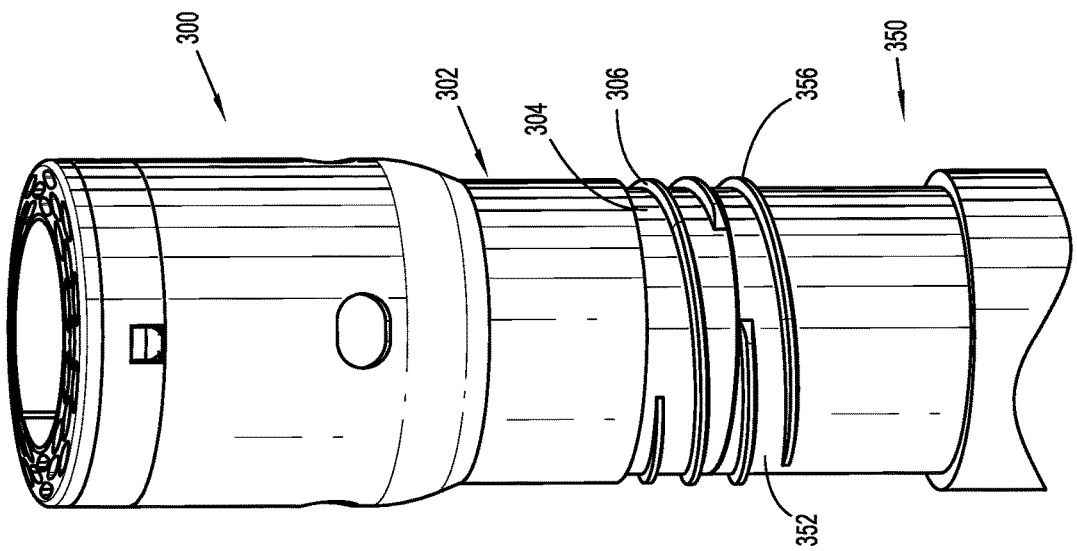
FIG. 21 is a perspective view of the replaceable loading unit and distal end of the adapter assembly shown in FIG. 19, with a collar member removed.

With reference initially to FIGS. 19-21, loading unit 300 is substantially similar to loading units 100 and 200 described hereinabove, and will only be described to the extent necessary to identify the differences therebetween. Loading unit 300 includes a shell member 302 configured to be received about flange 354 formed on distal end 352 of adapter assembly 350. Proximal end 304 of shell member 302 includes a thread portion 306 configured to be engaged by collar 360 that is operatively mounted on distal end 352 of adapter assembly 350.

Figure 22:
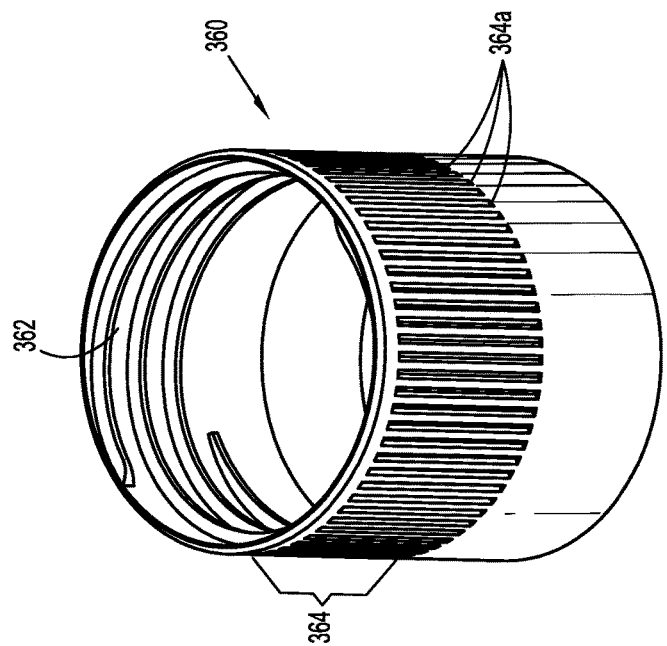
FIG. 22 is a perspective view of a collar member of the adapter assembly shown in FIG. 19.

With continued reference to FIGS. 19-21, distal end 352 of adapter assembly 350 includes flange 354 and a threaded portion 356. A shelf 358 is formed between flange 354 and threaded portion 356 of distal end 352 and is configured to engage a proximal surface 304a of proximal end 304 of shell member 302 of loading unit 300. Collar member 360, as shown in FIG. 22, is operatively mounted on distal end 352 of adapter assembly 350 (FIG. 19). Collar member 360 includes a threaded internal surface 362 configured to engage threaded portion 356 of distal end 352 of adapter assembly 350 and threaded portion 306 of proximal end 304 of shell member 302 of loading unit 300 when proximal end 304 of loading unit 300 is received about flange 354 of adapter assembly 350 and proximal surface 304a of proximal end 304 of shell member 302 abuts shelf 358 formed on distal end 352 of adapter assembly 350. An external portion 364 of collar member 360 may include ridges 364a or be otherwise configured to facilitate operable engagement by a user.

Figures 23, 24:
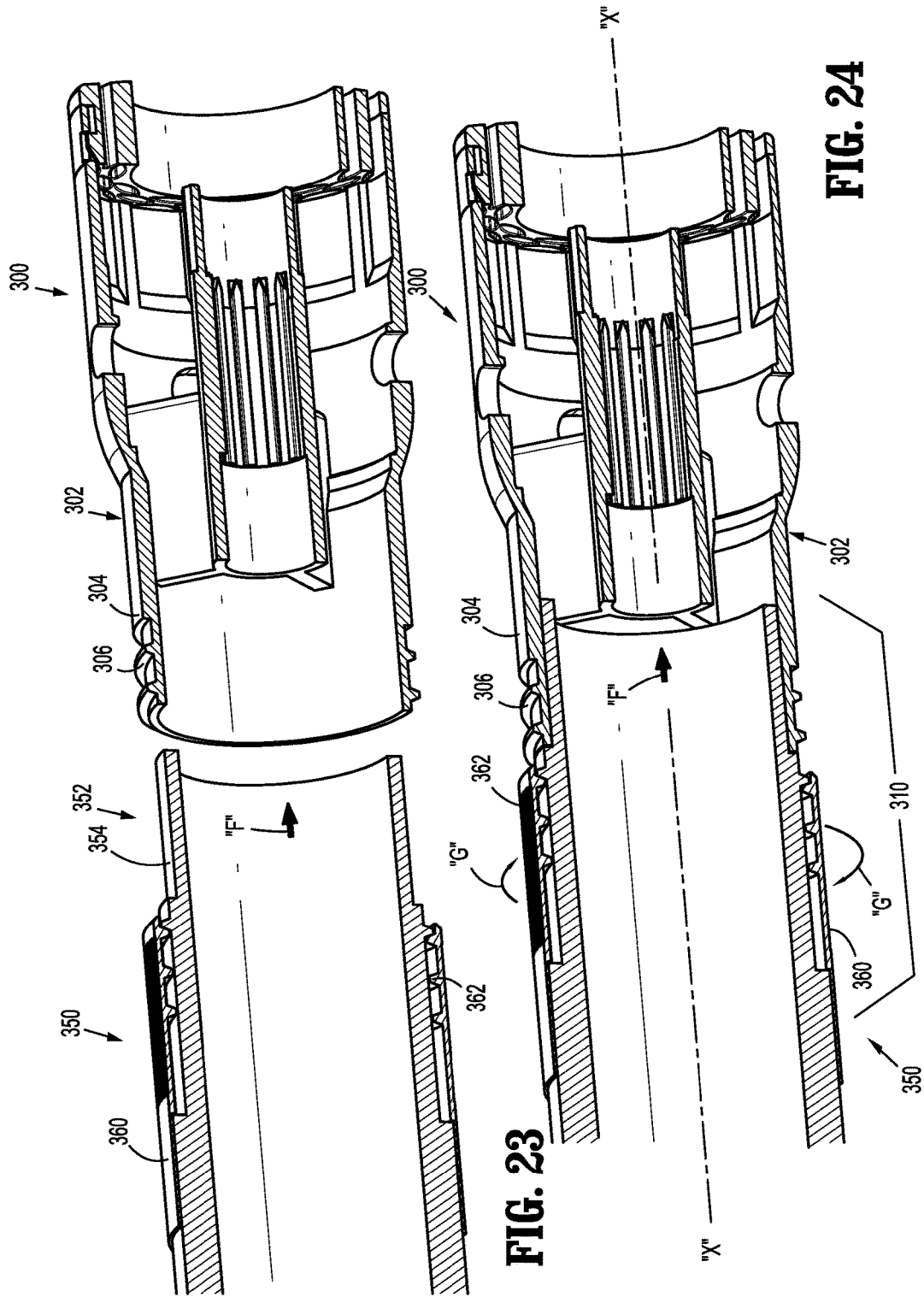
FIG. 23 is a cross-sectional side view of the replaceable loading unit shown in FIG. 19, with internal components removed, and a cross-sectional side view of the distal end of the adapter assembly shown in FIG. 19.
FIG. 24 is a cross-sectional side view of the replaceable loading unit shown in FIG. 23 partially attached to the distal end of adapter assembly shown in FIG. 23.

The operation of interlock assembly 310 will now be shown and described with reference to FIGS. 23-25. Referring initially to FIG. 23, distal end 352 of adapter assembly 350, and more particularly, flange 354, is aligned with proximal end 304 of shell member 302 of loading unit 300. Adapter assembly 350 is advanced relative to loading unit 300, as indicated by arrows "F" in FIGS. 23 and 24, such that flange 354 of adapter assembly 350 is received within proximal end 304 of shell member 302 of loading unit 300 and proximal surface 304a of shell member 302 abuts shelf 358 formed in distal end 352 of adapter assembly 350 (FIG. 24).

With reference to FIG. 24, once loading unit 300 is fully received about flange 354 of adapter assembly 350, i.e., when proximal surface 304a of proximal end 304 of shell member 302 of loading unit 300 abuts shelf 358 on distal end 352 of adapter assembly 350, collar 360 is rotated in a first direction relative to loading unit 300 and adapter assembly 350, about a longitudinal axis "X" of loading unit 300 and adapter assembly 350, as indicated by arrows "G" in FIG. 24, to cause threading engagement of internal threaded surface 362 of collar 360 with external threads 356 formed on distal end 352 of adapter assembly 350 and external threads 306 formed on proximal end 304 of shell member 302 of loading unit 300.

Figure 25:
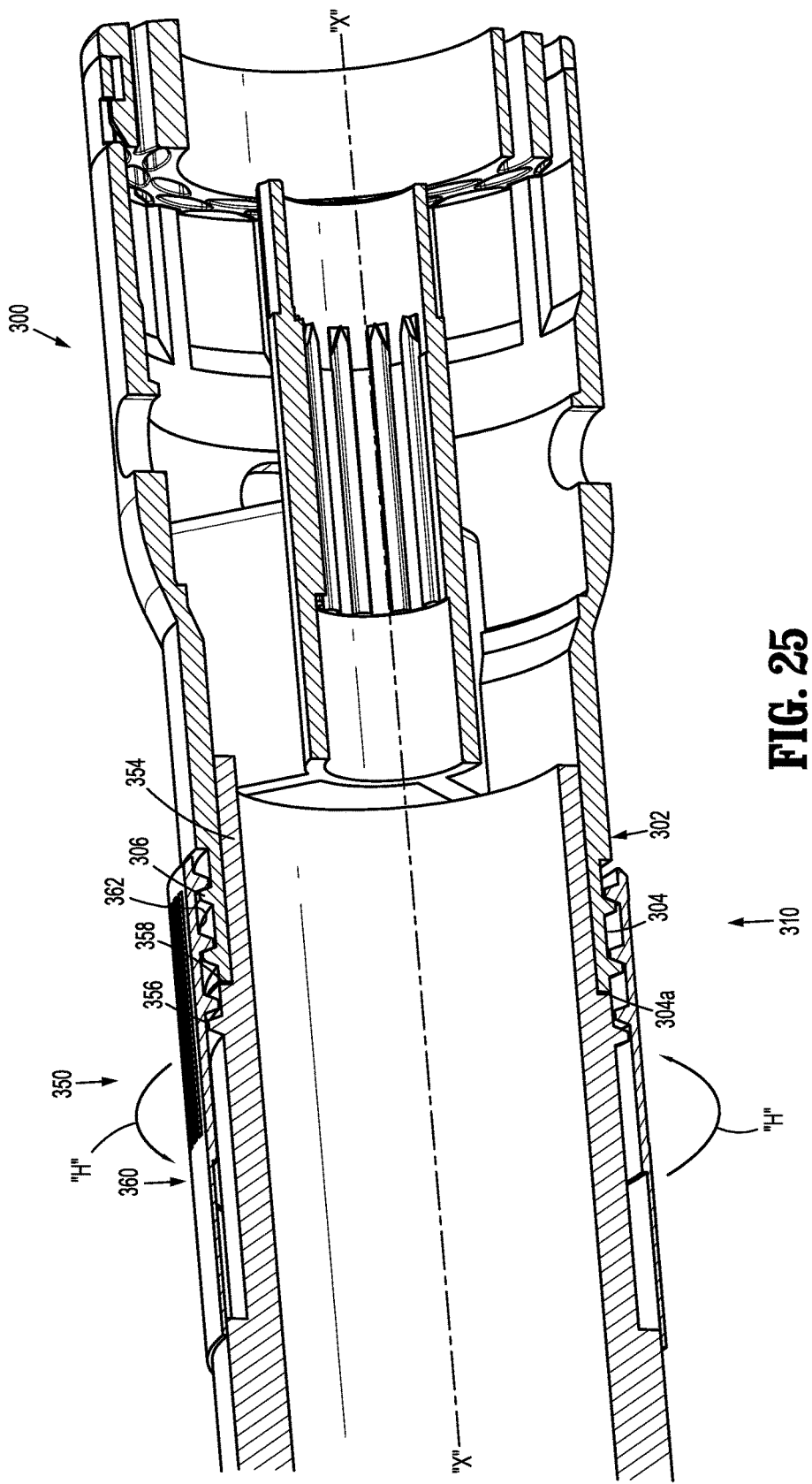
FIG. 25 is a cross-sectional side view of the replaceable loading unit shown in FIG. 23 attached to the distal end of adapter assembly shown in FIG. 23.

Turning to FIG. 25, engagement of internal threads 362 of collar 360 with external threads 356 on distal end 352 of adapter assembly 350 and external threads 306 on proximal end 304 of loading unit 300 secures loading unit 300 to adapter assembly 350. Loading unit 300 may be separated from adapter assembly 350 in the opposite manner of attachment. Specifically, collar 360 is rotated in a second direction relative to loading unit 300 and adapter assembly 350, about longitudinal axis "X" of loading unit 300 and adapter assembly 350, as indicated by arrows "H" in FIG. 25. Once internal threaded surface 362 of collar 360 is disengaged from external threads 306 formed on proximal end 304 of shell member 302 of loading unit 300, loading unit 300 separated from adapter assembly 350. One or more subsequent loading units 300 may be attached to and removed from adapter assembly 350 in the manner described above.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An interlock assembly for attaching a loading unit to a surgical stapling instrument, the interlock assembly comprising:
    a shell member having a proximal end defining a pair of openings and a distal end supporting a staple cartridge defining a plurality of staple retaining slots arranged in a pair of concentric rows; and
    an adapter assembly including a distal end securable to the proximal end of the shell member, the adapter assembly including a pair of arms each including a protrusion on a free end thereof, wherein each of the protrusions are received within the pair of openings when the distal end of the adapter assembly is received within the proximal end of the shell member.

2. The interlock assembly of claim 1, wherein the distal end of the adapter assembly defines a ledge configured to engage a proximal surface of the proximal end of the shell member when the distal end of the adapter assembly is received within the proximal end of the shell member to facilitate alignment of the pair of protrusions with the pair of openings.

3. The interlock assembly of claim 1, wherein the pair of arms are flexible radially inward.

4. The interlock assembly of claim 1, wherein the pair of arms are diametrically opposed.

5. The interlock assembly of claim 1, wherein the pair of protrusions of the adapter assembly extends through the pair of openings of the shell assembly when the distal end of the adapter assembly is received within the proximal end of the shell member.

6. A surgical stapling instrument including an interlock assembly, the surgical stapling instrument comprising:
    an elongate body portion having a distal end including first and second arms each including a protrusion on a free end thereof; and
    a shell member releasably secured to the elongate body portion, the shell member including a proximal end defining first and second openings and a distal end supporting a staple cartridge, wherein the protrusions of the elongate body portion are received within the first and second openings of the shell member when the shell member is received about the distal end of the elongate body portion to releasably secure the shell member to the elongate body portion.

7. The surgical stapling instrument of claim 6, wherein the distal end of the elongate body portion includes a ledge engaging a proximal surface of the proximal end of the shell member when the distal end of the elongate body portion is received within the proximal end of the shell member to facilitate alignment of the protrusions with the first and second openings.

8. The surgical stapling instrument of claim 6, wherein the first and second arms are flexible radially inward.

9. The surgical stapling instrument of claim 6, wherein the first and second arms are diametrically opposed.

10. The surgical stapling instrument of claim 6, wherein the pair of protrusions of the elongate body portion extends through the pair of openings of the shell member when the distal end of the elongate body portion is received within the proximal end of the shell member.

* * * * *